United States Patent [19]
Avellanet et al.

[11] Patent Number: 5,514,236
[45] Date of Patent: May 7, 1996

[54] METHOD OF MAKING FIBER-REINFORCED CATHETER INTRODUCER

[75] Inventors: Ernesto Avellanet, Miami Lakes, Fla.; Michael L. O'Hara, Salt Lake City, Utah

[73] Assignee: Cordis Corporation, Miami Lakes, Fla.

[21] Appl. No.: 213,835

[22] Filed: Mar. 17, 1994

Related U.S. Application Data

[63] Continuation of Ser. No. 947,704, Sep. 18, 1992, abandoned.

[51] Int. Cl.$^6$ .......................... B32B 31/06; B32B 31/16; B32B 31/26
[52] U.S. Cl. .......................... 156/154; 156/149; 156/294; 604/167; 604/282
[58] Field of Search .................. 156/153, 154, 156/149, 294; 604/158, 164, 167, 171, 244, 264, 280, 281, 282; 128/656, 657, 658, 772; 264/139, 162

[56] References Cited

U.S. PATENT DOCUMENTS

| | | | |
|---|---|---|---|
| 3,585,707 | 6/1971 | Stevens . | |
| 3,924,632 | 12/1975 | Cook | 604/282 |
| 4,000,739 | 1/1977 | Stevens . | |
| 4,321,226 | 3/1982 | Markling | 264/139 |
| 4,425,919 | 1/1984 | Alston et al. | 604/282 |
| 4,585,435 | 4/1986 | Vaillancourt | 604/27 |
| 4,634,432 | 1/1987 | Kocak . | |
| 4,705,511 | 11/1987 | Kocak . | |
| 4,764,324 | 8/1988 | Burnham | 264/173 |
| 4,863,442 | 9/1989 | De Mello et al. | 604/282 |
| 4,950,257 | 8/1990 | Hibbs et al. | 604/167 |
| 5,066,285 | 11/1991 | Hillstead | 604/164 |
| 5,078,702 | 1/1992 | Pomeranz | 604/280 |
| 5,114,408 | 5/1992 | Fleischhaker et al. | 604/167 |
| 5,120,323 | 6/1992 | Shockey et al. | 604/282 |
| 5,215,614 | 6/1993 | Wijkamp et al. | 156/153 |
| 5,221,270 | 6/1993 | Parker | 604/282 |
| 5,234,416 | 8/1993 | Macaulay et al. | 604/282 |
| 5,254,107 | 10/1993 | Soltesz | 604/282 |

*Primary Examiner*—Steven D. Maki
*Attorney, Agent, or Firm*—Gerstman, Ellis & McMillin, Ltd.

[57] ABSTRACT

An intravascular catheter introducer which comprises a tubular sheath having a distal end, for extending through the skin of a patient and into the vascular system. The sheath defines a lumen for receiving a catheter. A hub is carried on the proximal end of the sheath. The hub defines a bore communicating between the lumen and the exterior. A catheter-penetratable seal is carried in the bore, with the sheath carrying an embedded tubular reinforcing strand member along at least a majority of its length. Thus improved kink resistance is provided. Also, improved frictional characteristics are provided when the tubular sheath comprises polytetrafluoroethylene.

2 Claims, 2 Drawing Sheets

METHOD OF MAKING FIBER-REINFORCED CATHETER INTRODUCER

This application is a continuation of U.S. application Ser. No. 07/947,704, filed Sep. 18, 1992, now abandoned.

BACKGROUND OF THE INVENTION

Intravascular catheters such as angiographic catheters are introduced from the exterior of a patient into an artery or vein. After such introduction, the catheter is advanced or maneuvered through the arteriovenous system to a desired site, which may be an area of arteriostenosis, or an area from which x-ray contrast media is injected into the system, or the interior of the heart itself, for example. As described for example in the Stevens U.S. Pat. No. 4,000,739, such catheter may be emplaced by first inserting a hollow needle with a trocar through the skin into the lumen of the desired blood vessel. Following this, a guidewire is passed through the needle and advanced up the artery or vein toward the area or the organ to be studied. The needle can then be removed, leaving the guidewire in the vessel. Following this, a catheter introducer comprising a tubular sheath and a removable hollow stylet or dialator unit may be advanced together over the wire into the vessel. Then, the guidewire and the dilator unit are removed, leaving only the catheter introducer sheath present in the vessel.

Then, the desired catheter can be advanced through the sheath into the vessel.

A catheter introducer sheath carries a hub having hemostasis valve means on its proximal end to avoid uncontrolled bleeding and air embolism. The dilator unit, and then the catheter, pass through the hemostasis valve, which is typically a latex partition having a slit of well known design. Various designs of hemostasis valves and catheter introducers are in commercial use.

Problems with the prior art catheter introducers which have arisen include problems where the catheter sliding through the bore of the catheter introducer, and the catheter introducer itself in the artery or vein, exhibit undesirably high frictional characteristics. Catheters are advanced through emplaced catheter introducers a very substantial distance into the body to reach the heart or coronary arteries. Thus, it is distinctly undesirable for frictional problems between the catheter and catheter introducer to arise.

Another problem of prior art catheter introducers is that, of course, they must be of a minimum outer diameter to minimize the size of the incision in an artery. This requires the catheter introducer to be of as thin a wall as possible. However, thin-walled catheter introducers display a significant propensity for kinking. Also, it is desireable in many circumstances for the catheter introducer to be relatively stiff and will high hoop strength although flexible, and to have a distal tip which is materially softer and more flexible than the body of the catheter introducer.

In accordance with this invention, a reinforced catheter introducer is provided to exhibit substantial kink resistance coupled with the desired, resilient stiffness of the main body of the catheter introducer, and further coupled with a tapered, softer distal tip. The catheter introducer of this invention can also be of very low friction to solve frictional resistance problems which have been previously encountered in prior art catheter introducers.

DESCRIPTION OF THE INVENTION

In accordance with this invention an intravascular catheter introducer is provided which comprises a tubular sheath having a distal end for extending through the skin of a patient and into the vascular system. The sheath defines a lumen for receiving a catheter. The sheath and a hub are assembled such that the hub is carried on the proximal end of the sheath. The hub defines a bore communicating between the lumen and the exterior. Catheter-penetratable sealing means are carried in the bore. By this invention, the sheath carries embedded, tubular strand reinforcement means along at least a majority of its length.

Typically, the tubular sheath comprises polytetrafluoroethylene, or another similar low friction plastic for improvement of frictional characteristics of the catheter introducer of this invention.

Preferably, the tubular strand reinforcement means is positioned between and embedded in an inner plastic tube which is positioned within the tubular reinforcement means, and an outer plastic tube which is positioned outside of the tubular reinforcement means. The inner and outer plastic tubes typically extend distally beyond the tubular reinforcement means to define the sheath distal end at a position which is spaced from the tubular reinforcement means. The inner and outer plastic tubes are bonded together adjacent the distal end. Typically, the entire assembly is bonded together by means of high temperature fusing in a shaped die so that the inner and outer plastic tubes flow together into intimate bonding relation with each other and the tubular strand reinforcement means.

It is also preferred for the outer diameter of the sheath to be substantially constant from the distal end to the hub, even though a distal portion of the sheath is free of the strand reinforcement means. This can be accomplished by a grinding process after assembly and fusing of the inner and outer tubes with the tubular strand reinforcement, in which the outer diameter of the entire sheath is ground to a diameter constant with the diameter of the distal tip of the sheath. Thus, the thickness of the outer tubing is reduced along most the length of the catheter introducer sheath by an amount to compensate for thickness of the tubular strand reinforcement, so that the entire sheath may be of essentially constant outer diameter.

The hub of the catheter introducer of this invention may carry a side arm connection for fluid communication with the interior of the tubular sheath without having to pass through the catheter-penetratable sealing means. This structure is generally known to the art of catheter sheath introducers and may be of conventional design.

Additionally, it is preferred for the distal end of the sheath to define a tapered, annular, thin edge. This taper may be produced by grinding of the tip and it provides an improved transition that allows easier introduction of the catheter introducer, carried on a dilator unit, to easily enter the artery or vein.

DESCRIPTION OF SPECIFIC EMBODIMENTS

Figure 1:
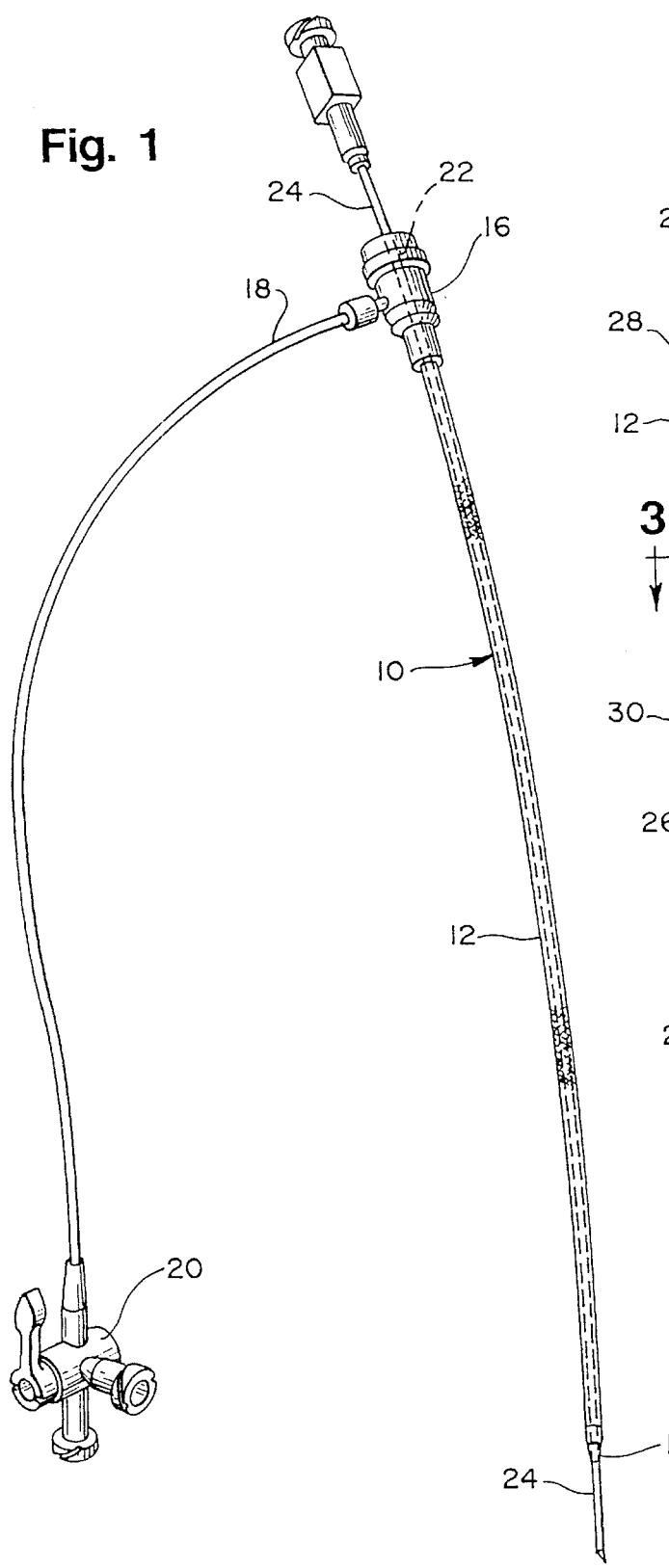
FIG. 1 is a perspective view of an arterial catheter introducer in accordance with this invention, shown to be carrying a guidewire.

Referring to the drawings, arterial catheter introducer 10 comprises a tubular sheath 12 having a distal end 14 which is tapered down to a feather edge tip, for improved ease in penetration through the skin along a dilator into an artery.

Catheter introducer 10 also carries a hub 16 at its proximal end which hub may be of conventional design, carrying a side arm and tube 18 terminating with a branched three way valve 20 and also defining a slotted latex partition valve 22 to permit sealing penetration of a guidewire, a dilator, and a catheter sequentially without significant back leakage. Hub 16 is typically of conventional design.

A conventional catheter 24 is shown to be extending through the length of catheter introducer 10, as a catheter does extend through introducer 10 as it is advanced into the artery and then forwardly on to a desired destination such as a site of arterial stenosis, or the heart itself. Typically, angiographic or angioplasty catheters may be advanced into arteries making use of a catheter introducer, which reduces damage to the artery and which facilitates the advancement and withdrawal of several catheters in succession.

Figure 2:
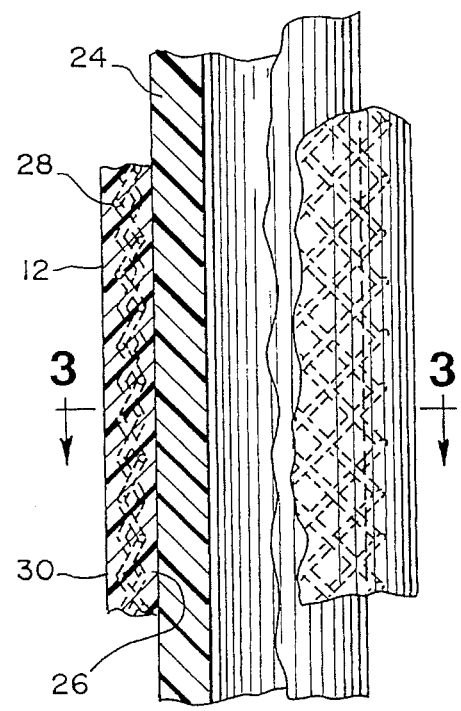
FIG. 2 is a fragmentary plan view, with portions broken away, showing a portion of the sheath of the catheter introducer and a catheter contained therein.
Figure 3:
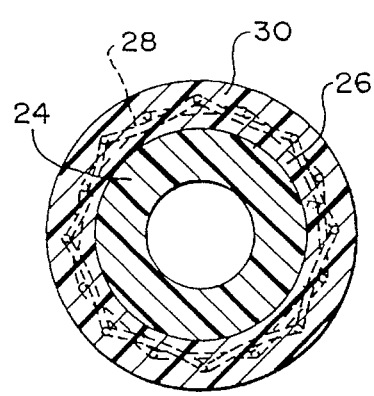
FIG. 3 is a sectional view taken along line 3—3 of FIG. 2.

As shown in FIGS. 2 and 3, catheter introducer sheath 12 in cross section defines an inner plastic tube 26, an embedded tubular strand reinforcement member 28, and an outer plastic tube 30, so that the tubular strand reinforcement means 28 is embedded between plastic tubes 26, 30 in intimately bonded relationship. This intimately bonded relationship may be created by heating the assembly of tubes 26, 30, and tubular strand reinforcement member 28 together at the softening point of the plastic to cause them to enter into intimate bonding.

The tubular strand reinforcement may be a standard woven or braided metal strand arrangement of the type that is conventionally used in catheters for reinforcement and stiffening of the catheter. The respective inner and outer tubes 26, 30 may either or both be made of polytetrafluoroethylene, which material provides a desired reduction in friction over other materials which have been used for catheter introducers, such as polyethylene.

Specifically, the sheath of this invention may be of a size to receive catheters of French 5 to 10 for example. The stainless steel braiding which comprises tubular sheath 28 may have a braid wire angle of 45 degrees, and a strand diameter of about 0.002 inch. Nylon may be used as another material for the strands rather than stainless steel.

Figure 4:
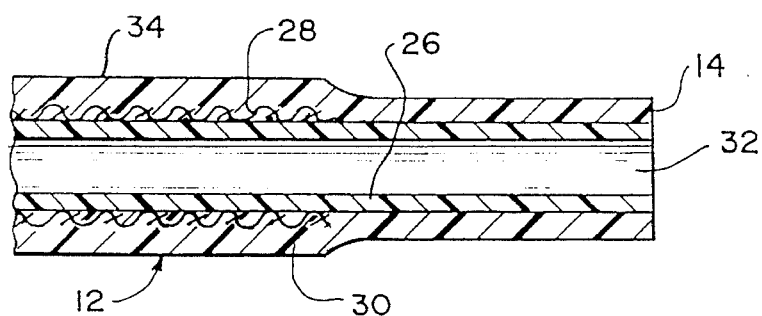
FIG. 4 is a fragmentary longitudinal sectional view of the distal tip of the intravascular catheter introducer of this invention in a position of intermediate manufacture.
Figure 5:
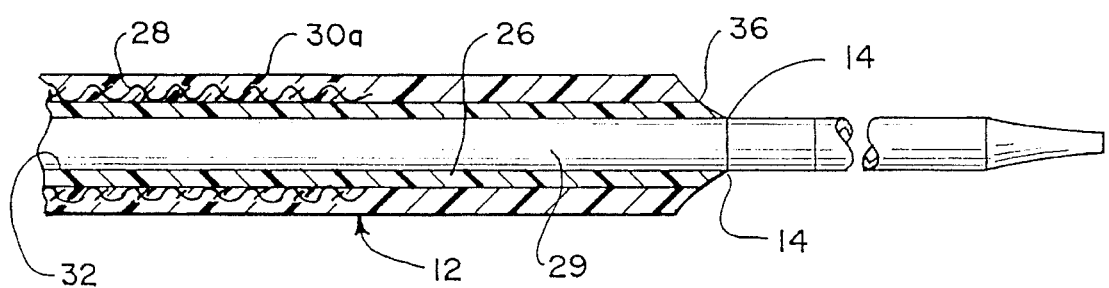
FIG. 5 is a longitudinal sectional view of the same portion of the catheter introducer as FIG. 4, after final processing is complete, the catheter introducer being shown to contain in its lumen an arterial catheter.

FIGS. 4 and 5 show an enlarged transverse sectional view of the catheter introducer of this invention and how it may be manufactured in its final stages. As shown in FIG. 4 and 5, the tubular strand reinforcement means 28 may be threaded over inner plastic tube 26 in such a manner that tubular strand reinforcement 28 terminates slightly short (thickly 0.3 to 1 centimeter) short of distal tip 14 of sheath 12. This may be performed on a silver mandrel 29 extending through the bore 32 of sheath 12. Then, outer tube 30 is placed over strand reinforcement tube 28 in the manner shown, with outer tube 30 extending to the distal end 14 along with tube 26.

As this assembly may be heated in a shape retaining die at a temperature of 700–750 degrees F when the plastic of tubes 26, 30 is polytetrafluoroethylene, to cause fusion bonding between the three parts.

Then, as indicated in FIG. 5, the sheath 12 can be given a constant outer diameter by grinding. As indicated in FIG. 4 the presence of fibrous tubular sheath 28 naturally enlarges to an extent the outer diameter of the proximal majority portion 34 of the catheter introducer. As FIG. 5 shows, this may be ground away to account for the extra width of the tubular braiding 28, while a thin portion 30a of outer tube 30 remains encasing the braiding 28.

Then, as shown in FIG. 5, the distal tip 14 may be ground into a frustoconical taper structure 36 to define a tapered, annular thin edge at the distal end 14. As stated above, this facilitates the penetration of the catheter introducer into the artery.

Thus, by this invention a catheter introducer is provided which exhibits greatly improved kink resistance, when compared with the non-reinforced catheter introducers of the prior art. The preferred polytetrafluoroethylene plastic used in the sheath provides significantly improved lubricity over prior designs of catheter introducers. Also, a frustoconical taper on the distal end leading to an annular, thin edge facilitates the insertion of the catheter introducer into an artery.

The above has been offered for illustrative purposes only, and is not intended to limit the scope of the invention of this application, which is as defined in the claims below.

That which is claimed is:

1. A method of making an intravascular catheter sheath introducer, which comprises the steps of:

(a) providing an inner plastic tube;

(b) providing an outer plastic tube;

(c) positioning a braided material between said inner plastic tube and said outer plastic tube such that the inner and outer plastic tubes extend distally beyond said braided material;

(d) heating said inner and outer plastic tubes to form a tubular sheath having an intimately bonded relationship between said inner and outer plastic tubes and said braided material wherein the braided material enlarges a proximal majority portion of the tubular sheath and the distal portion of the tubular sheath is free of the braided material;

(e) grinding the outer surface of said tubular sheath so that the tubular sheath has a substantially constant outer diameter; and (f) assembling the tubular sheath and a hub such that the hub is carried on the proximal end of said tubular sheath, said hub defining a bore communicating with the interior of the tubular sheath and having a catheter penetrable sealing valve carried in said bore and a side arm connection communicating with the interior of said tubular sheath.

2. A method as defined by claim 1, including the step of providing said tubular sheath with a tapered distal tip.

* * * * *